(12) United States Patent  (10) Patent No.: US 7,507,223 B2
Fontana  (45) Date of Patent: Mar. 24, 2009

(54) CANNULA FOR DISPENSING FLUID PRODUCTS FOR VAGINAL AND ANAL APPLICATIONS

(75) Inventor: Antonio Fontana, Carpi (IT)

(73) Assignee: LAMEPLAST S.p.A., Frazione Rovereto sul Secchia (IT)

( * ) Notice: Subject to any disclaimer, the term of this patent is extended or adjusted under 35 U.S.C. 154(b) by 232 days.

(21) Appl. No.: 10/569,082

(22) PCT Filed: Sep. 14, 2004

(86) PCT No.: PCT/EP2004/010257

§ 371 (c)(1), (2), (4) Date: Feb. 21, 2005

(87) PCT Pub. No.: WO2005/030313

PCT Pub. Date: Apr. 7, 2005

(65) Prior Publication Data

US 2006/0264802 A1   Nov. 23, 2006

(30) Foreign Application Priority Data

Sep. 26, 2003   (IT) ............................. MO03A0263

(51) Int. Cl.
 A61M 31/00 (2006.01)
 A61M 5/00 (2006.01)
 G01F 11/00 (2006.01)
(52) U.S. Cl. .................. 604/279; 604/60; 604/187; 604/224; 222/391
(58) Field of Classification Search ................ 604/279, 604/275, 264, 93.01, 39, 212
See application file for complete search history.

(56) References Cited

U.S. PATENT DOCUMENTS 2,712,315 A * 7/1955 Rice ............................ 604/60

(Continued)

FOREIGN PATENT DOCUMENTS

CH 199 616 A 8/1938

(Continued)

Primary Examiner—Nicholas D Lucchesi
Assistant Examiner—Ian K Holloway
(74) Attorney, Agent, or Firm—Browdy and Neimark, P.L.L.C.

(57) ABSTRACT

A cannula for dispensing fluid products for vaginal and anal applications comprising an inner tubular body for containing a fluid product, which is provided, at a first end, with an outlet for dispensing the product and, at a second end that lies opposite the first end, with a grip, at least one rectilinear longitudinal slot that is formed on the lateral surface of the inner tubular body, an outer tubular body, which is open at its two opposite ends and is fitted substantially coaxially over the inner tubular body and is associated therewith a rotary coupling, a helical guide formed on the inner lateral surface of the outer tubular body, a plunger, which is accommodated in the inner tubular body, with which it is associated so that it can slide axially, and is provided with at least one pin, which is inserted so that it can slide within the rectilinear longitudinal slot and is provided with an end that extends beyond the rectilinear longitudinal slot and couples to the helical guide, and removable elements for closing the outlet, the relative rotation of the inner tubular body and of the outer tubular body being adapted to move the plunger so that it slides along the inner tubular body in order to expel the product from the outlet.

22 Claims, 4 Drawing Sheets

U.S. PATENT DOCUMENTS

| | | | |
|---|---|---|---|
| 3,902,621 A * | 9/1975 | Hidding | 215/252 |
| 4,900,315 A | 2/1990 | Lundqvist et al. | |
| 5,234,136 A * | 8/1993 | Kopis | 222/391 |
| 6,436,379 B1 * | 8/2002 | Hill et al. | 424/61 |

FOREIGN PATENT DOCUMENTS

| | | |
|---|---|---|
| DE | 365 710 C | 12/1922 |
| EP | 0 224 387 A | 6/1987 |
| FR | 1 179 779 A | 5/1959 |
| FR | 1 231 235 A | 9/1960 |
| FR | 1 288 915 A | 3/1962 |

* cited by examiner

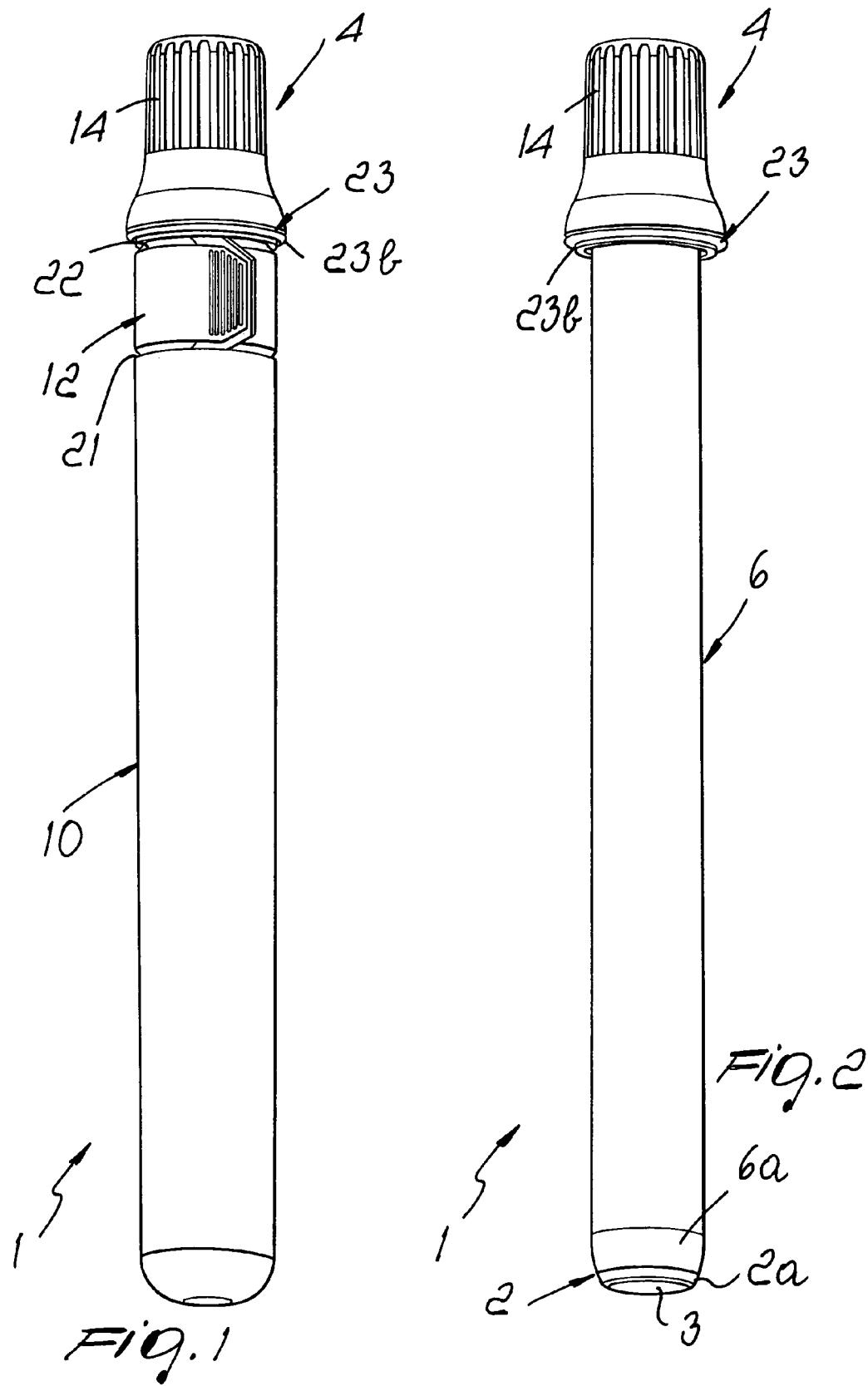

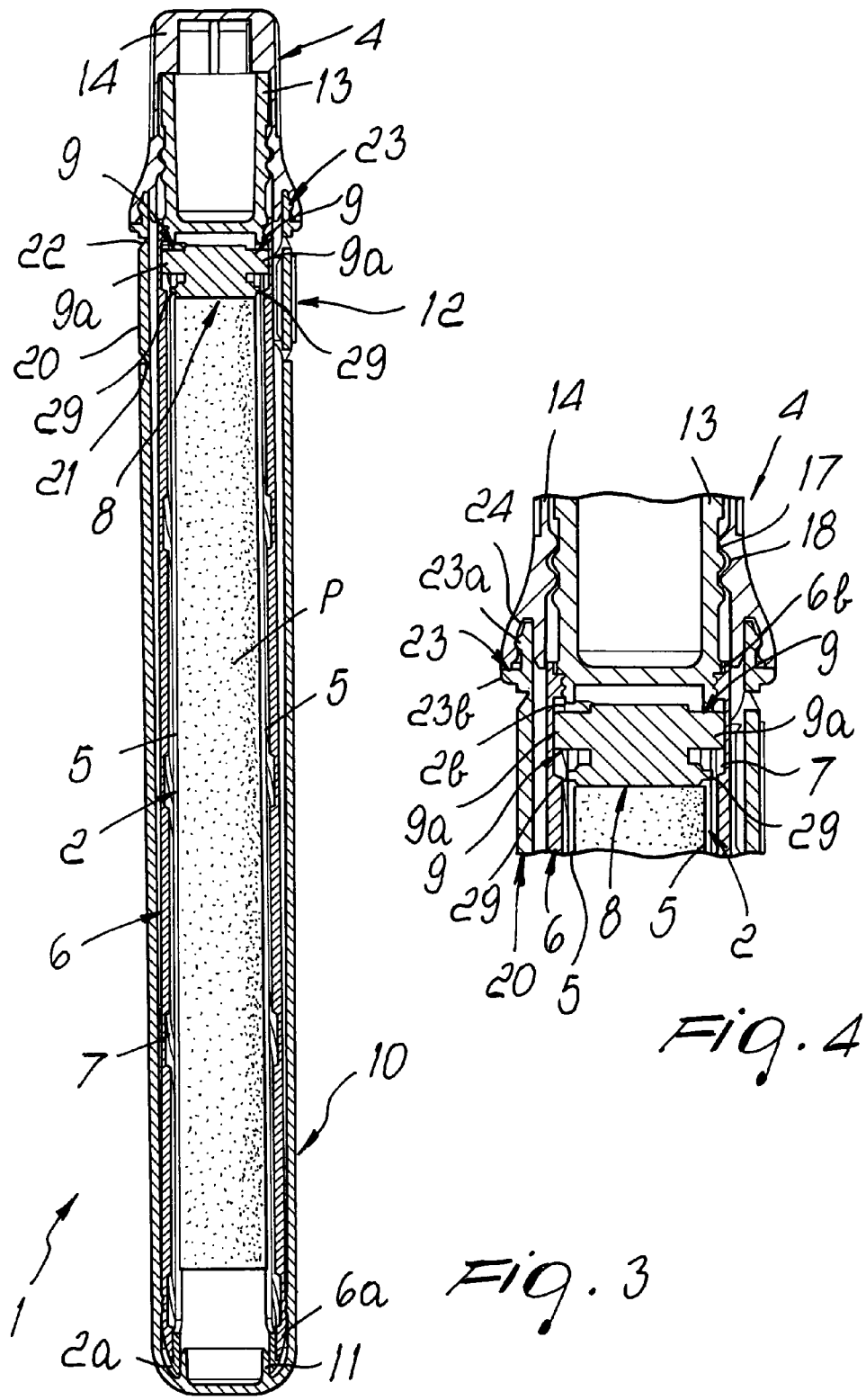

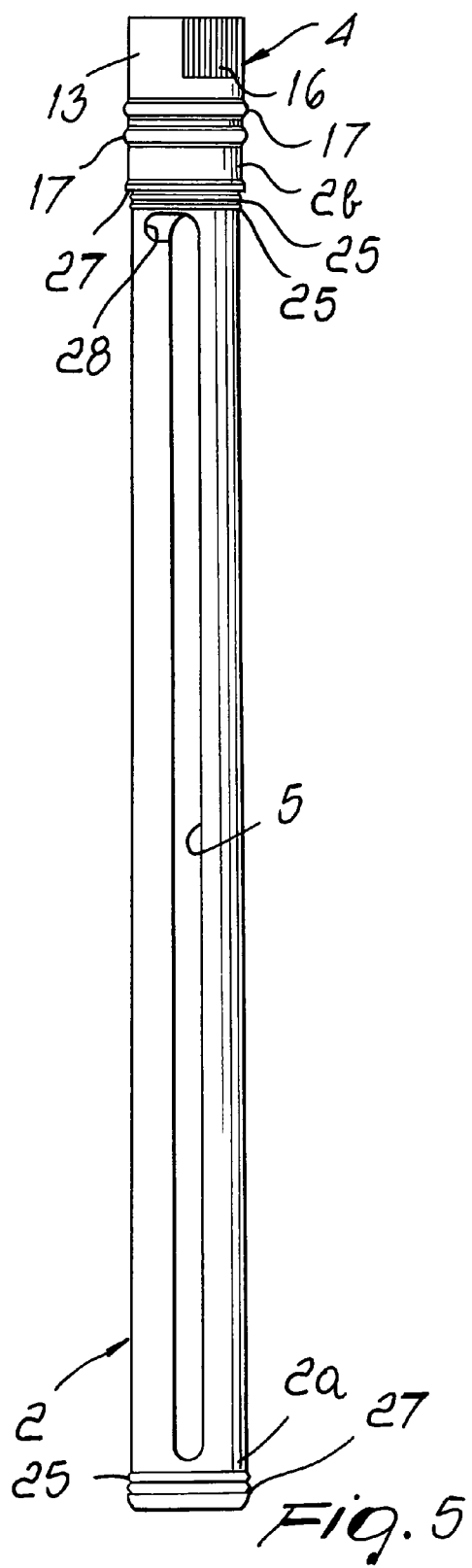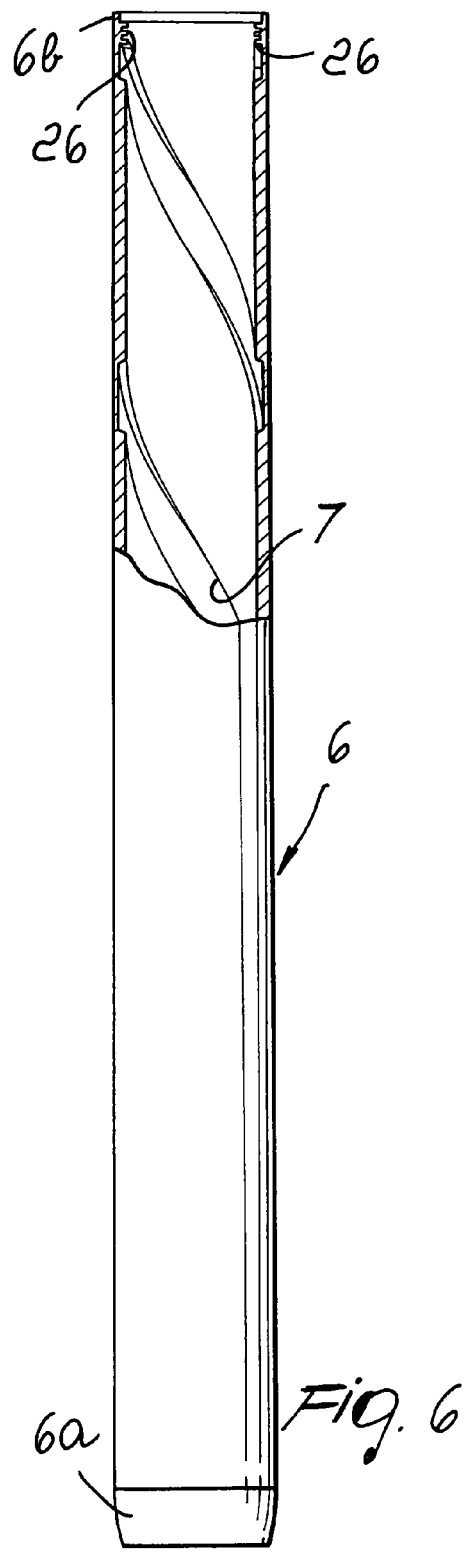

CANNULA FOR DISPENSING FLUID PRODUCTS FOR VAGINAL AND ANAL APPLICATIONS

The present invention relates to a cannula for dispensing fluid products for vaginal and anal applications, particularly for the application of ointments, creams, medicinal pastes, or the like.

BACKGROUND OF THE INVENTION

Cannulas for dispensing fluid medicinal products are known which are used in particular for vaginal and anal applications and are generally sold in packages together with tubes or bottles containing one of said products.

Known cannulas are constituted by a barrel that is suitable to contain the product and inside which a plunger, rigidly coupled to the end of a pusher rod, can slide.

The barrel has an open end, which can be coupled to the dispensing outlet of the tube in order to introduce in said barrel the amount of product to be applied, and through which the introduced product is dispensed.

The opposite end of the barrel is closed by a back wall, which is provided with a hole in which the pusher rod is inserted slidingly; said back wall acts as an element for stopping the plunger in order to prevent its extraction.

The product introduced in the cannula is dispensed by acting on the pusher rod in the direction in which the plunger slides toward the open end of the barrel.

Cannulas are also known which are constituted by a barrel, which has open opposite ends and inside which a plunger is inserted slidingly, and by a pusher rod, which is separate from the plunger and can be coupled detachably thereto.

Undercuts or shoulders for abutment are formed at the opposite ends of the barrel and are suitable to stop the sliding of the plunger, preventing it from being extracted under the action of the pusher rod.

These last cannulas can be sold in packages that contain a single pusher rod, a plurality of empty single-use barrels to be used for the various applications, and one or more tubes of product.

In this case, one of the two ends of the barrels can be coupled to the dispensing outlet of the tube in order to introduce the product in the barrels, while the opposite end acts as a passage for the pusher rod.

As an alternative, the cannulas can be sold in packages that contain a single pusher rod and a plurality of barrels that are already filled with the product to be applied and are provided, at their two opposite ends, with closure plugs that are removed upon use.

However, these known cannulas are not free from drawbacks, including the fact that they have a significant space occupation, which makes them difficult and awkward to handle for users.

Another drawback of known cannulas, particularly those constituted by a rod that is detachably associable with the plunger, is that they are not straightforward and ready to use for users, since they in fact require additional assembly operations.

Another drawback of known cannulas is that the sliding of the plunger under the thrust applied to the rod often causes an uncontrolled dispensing of amounts of product that are unwanted because they are excessive or insufficient for the actual requirements.

SUMMARY OF THE INVENTION

The aim of the present invention is to eliminate the drawbacks noted above of known cannulas, by providing a cannula for dispensing fluid products for vaginal and anal applications that is compact, is simple and straightforward to use on the part of users, and allows controlled and gradual dispensing of the product.

Within this aim, an object of the present invention is to provide a cannula for dispensing fluid products that is simple, relatively easy to provide in practice, safe in use, effective in operation, and has a relatively low cost.

This aim and this and other objects that will become better apparent hereinafter are achieved by a cannula for dispensing fluid products for vaginal and anal applications, characterized in that it comprises an inner tubular body for containing a fluid product, which is provided, at a first end, with an outlet for dispensing said product and, at a second end that lies opposite the first end, with a grip, at least one rectilinear longitudinal slot that is formed on the lateral surface of said inner tubular body, an outer tubular body, which is open at its two opposite ends and is fitted substantially coaxially over said inner tubular body and is associated therewith a rotary coupling, a helical guide formed on the inner lateral surface of said outer tubular body, and a plunger, which is accommodated in said inner tubular body, with which it is associated so that it can slide axially, and is provided with at least one pin, which is inserted so that it can slide within said rectilinear longitudinal slot and is provided with an end that extends beyond said rectilinear longitudinal slot and couples to said helical guide, the relative rotation of said inner tubular body and of said outer tubular body being suitable to move said plunger so that it slides along said inner tubular body in order to expel said product from said outlet.

BRIEF DESCRIPTION OF THE DRAWINGS

Further characteristics and advantages of the present invention will become better apparent from the following detailed description of a preferred but not exclusive embodiment of a cannula for dispensing fluid products for vaginal and anal applications, illustrated by way of non-limiting example in the accompanying drawings, wherein:

FIG. 1 is a perspective view of the cannula according to the invention, in the closed packaging configuration;

FIG. 2 is a perspective view of the cannula according to the invention, in the open configuration for use;

FIG. 3 is a schematic sectional view of the cannula according to the invention, in the closed packaging configuration;

FIG. 4 is an enlarged-scale view of a detail of the cannula of FIG. 3;

FIG. 5 is a schematic view of the inner tubular body of the cannula according to the invention;

FIG. 6 is a partially sectional schematic view of the outer tubular body of the cannula according to the invention;

DESCRIPTION OF THE PREFERRED EMBODIMENTS

Figure 7:
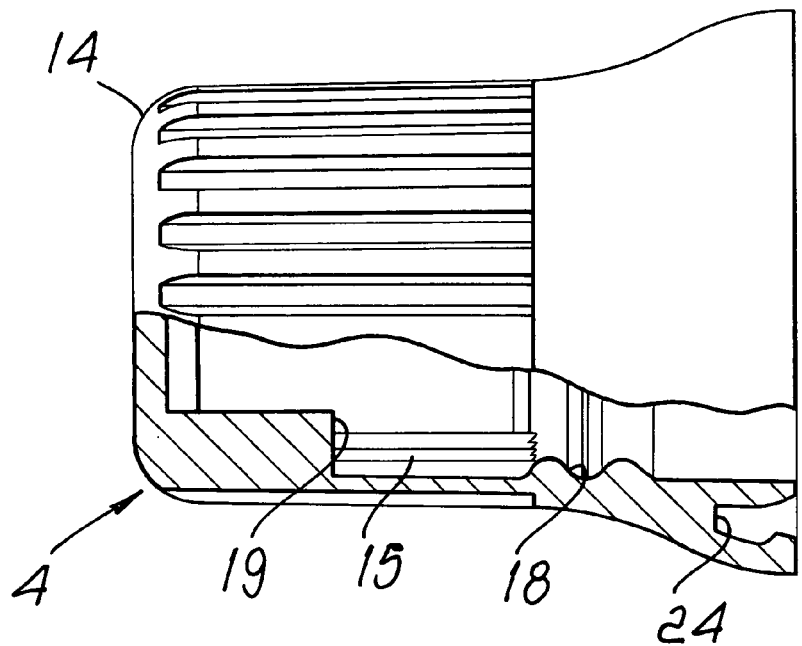
FIG. 7 is a partially sectional schematic view of a detail of the grip of the cannula according to the invention.
Figure 8:
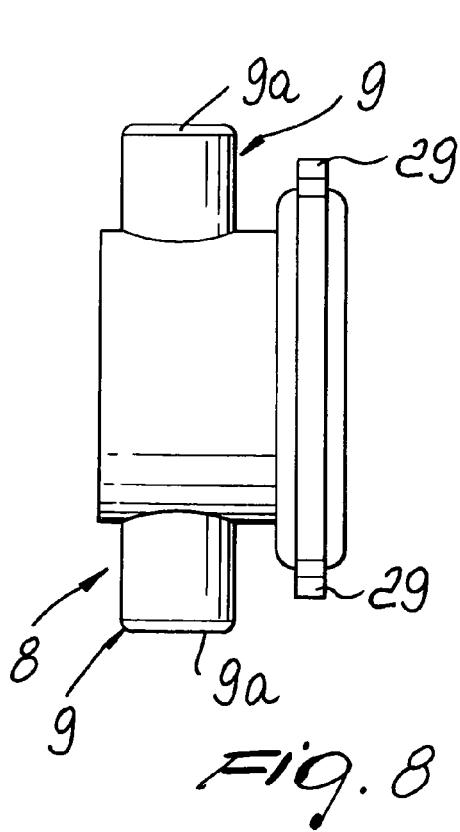
FIG. 8 is a side view of the plunger of the cannula according to the invention.
Figure 9:
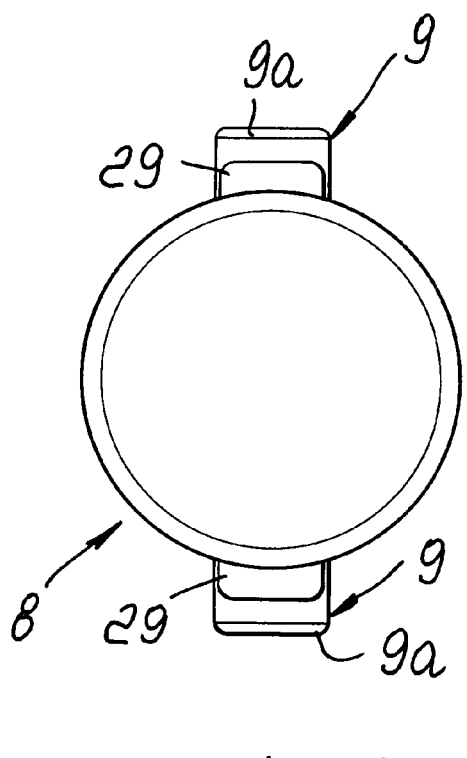
FIG. 9 is a front view of the plunger of the cannula according to the invention.

With reference to the figures, the reference numeral 1 generally designates a cannula for dispensing fluid products P for vaginal and anal applications, particularly for the application of ointments, creams, medicinal pastes, or the like.

The cannula 1 comprises an inner tubular body 2 for containing the product P, which is provided, at a first end 2a, with an outlet 3 for dispensing the product P and, at a second end 2b that lies opposite the first end, with a grip 4; at least one and preferably two longitudinal and rectilinear mutually diametrically opposite slots 5 are formed on the lateral surface of the inner tubular body 2.

An outer tubular body 6 is fitted substantially coaxially over the inner tubular body 2, is open at its two opposite ends 6a and 6b, and is associated with the inner tubular body 2 with a rotary coupling; on the inner lateral surface of the outer tubular body 6 there is a helical guide 7, which is shaped like a groove and lies between the two opposite ends 6a and 6b.

A plunger 8 is accommodated within the inner tubular body 2, with which it is associated so that it can slide axially; the plunger 8 is provided with at least one and preferably two mutually diametrically opposite pins 9, which can be inserted so that they can slide in a respective slot 5 and are provided with a respective end 9a that extends beyond the slots 5 to couple by sliding within the helical guide 7.

The cannula 1 further comprises detachable means for closing the outlet 3, which can be constituted for example by a sheath 10 fitted over the outer tubular body 6; the sheath 10 is of the tubular type, with an open end, for the insertion and extraction of the outer tubular body 6 in it and from it, and an opposite end that is closed and at which an internal plug 11 for closing the outlet 3 is formed.

The grip 4 and the sheath 10 are mutually anchored temporarily by tamper-resistant sealing means 12 of the tear-off type.

The grip 4 comprises a tang 13, which is formed at the second end 2b of the inner tubular body 2 and protrudes beyond the outer tubular body 6, and a cap 14, which is fitted monolithically over the tang 13.

Between the tang 13 and the cap 14 there are means for coupling their relative rotation and means for coupling their relative axial sliding.

The means for coupling the relative rotation between the tang 13 and the cap 14 can be of the type of a side-fit coupling or the like, and can be constituted for example by a plurality of knurlings 15, which are arranged longitudinally on at least one portion of the inner lateral surface of the cap 14 and mesh with corresponding knurlings 16 formed on a respective portion of the outer lateral surface of the tang 13; advantageously, the portions are two and are mutually diametrically opposite.

The means for coupling the relative axial sliding between the tang 13 and the cap 14 can be of the interlocking type and can be constituted for example by rings 17, which protrude from the outer lateral surface of the tang 13 and couple by interlocking with corresponding annular grooves 18 formed on the inner lateral surface of the cap 14.

A locator abutment 19 for the tang 13 is further provided inside the cap 14.

The cap 14 is accordingly rigidly coupled to the tang 13 and therefore to the inner tubular body 2.

The tamper-resistant sealing means 12 comprise a tab 20, which can be removed by tearing, is wrapped around the outer tubular body 6, and is associated, along respective tear lines 21 and 22 formed along its opposite longitudinal edges, with the sheath 10 and with a strip 23 that is rigidly coupled to the grip 4.

The strip 23 comprises a fixing flap 23a, which is rigidly coupled to the perimetric edge of the grip 4, for example by interlocking in a seat 24 that is formed along the perimetric edge of the cap 14, and an indicator flap 23b, which remains arranged so that it protrudes from the grip 4 (seat 24) to indicate that the cannula 1 has been opened.

As an alternative, the fixing flap 23a might be rigidly coupled to the grip 4 by means of systems other than interlocking, for example by gluing, welding, ultrasonic welding, or others.

Means for sealing the product P are formed between the inner tubular body 2 and the outer tubular body 6 and can be constituted for example by sealing rings 25, which are formed at the first end 2a and at the second end 2b of the inner tubular body 2 and are suitable to mate with corresponding containment channels 26 formed at the opposite ends 6a and 6b of the outer tubular body 6.

At the first end 2a and at the second end 2b of the inner tubular body 2 there are shoulders 27 for the abutment of the opposite ends 6a and 6b, respectively, of the outer tubular body 6.

The stroke of the plunger 8 is limited by grooves 28 for stopping the pins 9, which are formed at the opposite ends of the slots 5 substantially transversely thereto.

The plunger 8 further comprises two scrapers 29 for cleaning the slots 5, which are formed so that they are mutually diametrically opposite and protrude on its outer lateral surface and, taking as reference the direction in which the plunger 8 slides toward the dispensing outlet 3, downstream of the pins 9.

The scrapers 29 are inserted so that they can slide in the slots 5, and advantageously they have a polygonal transverse cross-section and their height is less than, or equal to, the thickness of the inner tubular body 2.

The cannula 1 is sold in the closed packaging configuration (FIGS. 1 and 3), filled with the product P; in this configuration, the sheath 10 is fitted over the outer tubular body 6 so as to close the outlet 3 and is temporarily anchored, by way of the tamper-resistant sealing means 12, to the grip 4, while the plunger 8 is arranged at the beginning of its stroke proximate to the tang 13.

By removing the tab 20, the sheath 10 is disengaged from the grip 4, while the strip 23 remains coupled to the cap 14, with the indicator flap 23b that protrudes from it so as to indicate that first opening has occurred.

By sliding off the sheath 10, the outlet 3 is connected to the outside and the cannula 1 is in the open configuration for use, ready for application of the product P (FIG. 2).

For application, it is sufficient to act on the grip 4, keeping the outer tubular body 6 stationary, in order to turn the inner tubular body 2 with respect to the outer tubular body 6; as a consequence of this relative rotation, the resulting force that acts on the pins 9, rigidly coupled so that they slide along the slots 5 and along the helical guide 7, moves the plunger 8 so that it slides axially along the inner tubular body 2 to expel the product P from the outlet 3.

In practice, it has been found that the described invention achieves the intended aim and object.

The cannula according to the invention is in fact compact, particularly with respect to known cannulas provided with a pusher rod, and this compactness makes it easier to handle.

Moreover, the cannula according to the invention is simple and straightforward to use, and thanks to the thrust applied to the plunger as a consequence of the relative rotary motion imparted by the user to the inner tubular body with respect to the outer tubular body, it allows better control and graduality of the dispensing of the product packaged therein.

The invention thus conceived is susceptible of numerous modifications and variations, all of which are within the scope of the appended claims.

All the details may further be replaced with other technically equivalent ones.

In practice, the materials used, as well as the shapes and the dimensions, may be any according to requirements without thereby abandoning the scope of the appended claims.

The disclosures in Italian Patent Application No. M02003A000263 from which this application claims priority are incorporated herein by reference.

What is claimed is:

1. A cannula for dispensing fluid products for vaginal and anal applications, comprising an inner tubular body for containing a fluid product, which is provided, at a first end, with an outlet for dispensing said product and, at a second end that lies opposite the first end, with a grip at least one rectilinear longitudinal slot that is formed on the lateral surface of said inner tubular body, and outer tubular body, which is open at its two opposite ends and is fitted substantially coaxially over said inner tubular body and is associated therewith a rotary coupling, a helical guide formed on an inner lateral surface of said outer tubular body, and a plunger which is accommodated in said inner tubular body, with which it is associated so that it can slide axially, and is provided with at least one pin which is inserted so that it can slide within said rectilinear longitudinal slot and is provided with an end that extends beyond said rectilinear longitudinal slot and couples to said helical guide, the relative rotation of said inner tubular body and of said outer tubular body being adapted to move said plunger so that t slides along said inner tubular body in order to expel said product from said outlet;

wherein said grip comprises a tang fixed to and extending into the said second end of the inner tubular body and rotatably engaged to said outer tubular body and a cap fixed to said tang and over one end of said outer tubular body by a plurality of first knurlings, which run longitudinally on at least one portion of the inner lateral surface of said cap and mesh with corresponding second knurlings formed on a respective portion of the outer lateral surface of said tang to preclude rotation between said cap and said tang, and at least one ring that protrudes from said outer lateral surface of the tang and is coupled by interlocking with a corresponding annular groove formed in said inner lateral surface of the cap to preclude relative sliding along the length of the cannula between said cap and said tang.

2. The cannula of claim 1, wherein means for sealing said product are formed between said inner tubular body and said outer tubular body.

3. The cannula of claim 2, wherein said sealing means comprise at least one sealing ring, which is formed at said first and second ends of said inner tubular body and is adapted to couple to a corresponding containment channel formed at said opposite ends of said outer tubular body.

4. The cannula of claim 3, wherein said first and second ends of the inner tubular body comprise abutment shoulders, respectively for the opposite ends of said outer tubular body.

5. The cannula of claim 1, wherein said rectilinear longitudinal slots are two and are mutually diametrically opposite, said plunger being provided with respective two of said pins, which are mutually diametrically opposite.

6. The cannula of claim 5, further comprising grooves for stopping the stroke of said plunger, which are formed at the opposite ends of said rectilinear longitudinal slots and substantially transversely thereto.

7. The cannula of claim 6, wherein said plunger comprises at least one scraper, which is formed downstream of said pin, in the direction for sliding toward said outlet, and is inserted in said rectilinear longitudinal slot.

8. The cannula of claim 7, wherein said scraper has a polygonal transverse cross-section.

9. The cannula of claim 7, wherein the height of said scraper is less than, or equal to, the thickness of said inner tubular body.

10. The cannula of claim 7, wherein said scrapers are two and are mutually diametrically opposite.

11. The cannula of claim 1, wherein said helical guide is formed by a groove that lies between the opposite ends of said outer tubular body.

12. A cannula for dispensing fluid products for vaginal and anal applications, comprising an inner tubular body for containing a fluid product, which is provided, at a first end, with an outlet for dispensing said product and, at a second end that lies opposite the first end, with a grip at least one rectilinear longitudinal slot that is formed on the lateral surface of said inner tubular body, and outer tubular body, which is open at its two opposite ends and is fitted substantially coaxially over said inner tubular body and is associated therewith a rotary coupling, a helical guide formed on an inner lateral surface of said outer tubular body, and a plunger which is accommodated in said inner tubular body, with which it is associated so that it can slide axially, and is provided with at least one pin which is inserted so that it can slide within said rectilinear longitudinal slot and is provided with an end that extends beyond said rectilinear longitudinal slot and couples to said helical guide, the relative rotation of said inner tubular body and of said outer tubular body being adapted to move said plunger so that it slides along said inner tubular body in order to expel said product from said outlet;

wherein said grip comprises a tang fixed to and extending into said second end of the tubular body and rotatably engaged to said outer tubular body and a cap fixed to said tang and over one end of said tubular body;

wherein a sheath extending over said tubular body has a first end having a plug inserted into said dispensing outlet of said inner tubular body and a second end engaged to a tamper-resistant sealing tab;

wherein said sealing tab encircles said outer tubular body and is engaged along respective tear lines along opposite longitudinal edges thereof to said second end of said sheath and a bottom edge of said cap so that the outer tubular body is entirely enclosed within the cannula; and wherein when said sealing tab is removed to disengage said sheath from over said outer tubular body, an indicator flap is exposed.

13. The cannula of claim 12, wherein means for sealing said product are formed between said inner tubular body and said outer tubular body.

14. The cannula of claim 13, wherein said sealing means comprise at least one sealing ring, which is formed at said first and second ends of said inner tubular body and is adapted to couple to a corresponding containment channel formed at said opposite ends of said outer tubular body.

15. The cannula of claim 14, wherein said first and second ends of the inner tubular body comprise abutment shoulders, respectively for the opposite ends of said outer tubular body.

16. The cannula of claim 12, wherein said rectilinear longitudinal slots are two and are mutually diametrically opposite, said plunger being provided with respective two of said pins, which are mutually diametrically opposite.

17. The cannula of claim 16, further comprising grooves for stopping the stroke of said plunger, which are formed at the opposite ends of said rectilinear longitudinal slots and substantially transversely thereto.

18. The cannula of claim 17, wherein said plunger comprises at least one scraper, which is formed downstream of said pin, in the direction for sliding toward said outlet, and is inserted in said rectilinear longitudinal slot.

19. The cannula of claim 18, wherein said scraper has a polygonal transverse cross-section.

20. The cannula of claim 18, wherein the height of said scraper is less than, or equal to, the thickness of said inner tubular body.

21. The cannula of claim 18, wherein said scrapers are two and are mutually diametrically opposite.

22. The cannula of claim 12, wherein said helical guide is formed by a groove that lies between the opposite ends of said outer tubular body.

* * * * *